(12) United States Patent
Mattison (10) Patent No.: US 7,338,509 B2
(45) Date of Patent: Mar. 4, 2008

(54) ELECTROACTIVE POLYMER ACTUATED SHEATH FOR IMPLANTABLE OR INSERTABLE MEDICAL DEVICE

(75) Inventor: Richard Carlton Mattison, Zimmerman, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 754 days.

(21) Appl. No.: 10/702,314

(22) Filed: Nov. 6, 2003

(65) Prior Publication Data

US 2005/0102017 A1 May 12, 2005

(51) Int. Cl.
*A61M 29/00* (2006.01)
(52) U.S. Cl. ...................................................... 606/192
(58) Field of Classification Search ................ 606/191, 606/192, 194, 195, 198, 41, 42, 32; 623/1.11, 623/1.12
See application file for complete search history.

(56) References Cited

U.S. PATENT DOCUMENTS

| | | | | |
|---|---|---|---|---|
| 5,100,933 | A | 3/1992 | Tanaka et al. | 523/300 |
| 5,250,167 | A | 10/1993 | Adolf et al. | 204/299 R |
| 5,268,082 | A | 12/1993 | Oguro et al. | 204/282 |
| 5,389,222 | A | 2/1995 | Shahinpoor | 204/299.2 |
| 5,556,700 | A | 9/1996 | Kaneto et al. | 428/332 |
| 5,631,040 | A | 5/1997 | Takuchi et al. | 427/100 |
| 5,665,103 | A * | 9/1997 | Lafontaine et al. | 606/192 |
| 5,766,013 | A | 6/1998 | Vuyk | 434/114 |
| 5,855,565 | A | 1/1999 | Bar-Cohen et al. | 604/104 |
| 6,109,852 | A | 8/2000 | Shahinpoor et al. | 414/1 |
| 6,117,296 | A | 9/2000 | Thomson | 204/607 |
| 6,249,076 | B1 | 6/2001 | Madden et al. | 310/363 |
| 6,264,671 | B1 | 7/2001 | Stack et al. | 606/198 |
| 6,391,051 | B2 | 5/2002 | Sullivan, III et al. | 623/1.12 |
| 6,447,540 | B1 | 9/2002 | Fontaine et al. | 623/1.12 |
| 6,475,639 | B2 | 11/2002 | Shahinpoor et al. | 428/614 |
| 6,514,237 | B1 | 2/2003 | Maseda | 604/533 |
| 6,520,983 | B1 | 2/2003 | Colgan et al. | 623/1.11 |
| 2001/0001833 | A1 | 5/2001 | Ravenscroft et al. | 623/1.12 |
| 2001/0026165 | A1 | 10/2001 | Pelrine et al. | 324/750 |
| 2002/0039620 | A1 | 4/2002 | Shahinpoor et al. | 427/2.12 |
| 2003/0069474 | A1 | 4/2003 | Couvillon, Jr. | 600/152 |

FOREIGN PATENT DOCUMENTS

WO    WO 01/58973 A2    8/2001

OTHER PUBLICATIONS

Jager, Edwin W.H., et al., "Applications of Polypyrrole Microactuators," SPIE Proceedings, Conference on Electroactive Polymer Actuators and Devices, Mar. 1999, vol. 3669, pp. 377-384.

(Continued)

*Primary Examiner*—Kevin T. Truong
(74) *Attorney, Agent, or Firm*—Mayer & Williams PC; David B. Bonham, Esq.; Keum J. Park, Esq.

(57) ABSTRACT

A medical device delivery sheath, which comprises an active member that volumetrically expands and contracts upon application of an appropriate electrical potential. The active member further comprises an electroactive polymer, for example, polypyrrole. Also described is a medical device delivery system comprising the same, as well as a method of delivering a medical device using the same.

23 Claims, 4 Drawing Sheets

OTHER PUBLICATIONS

Otero, Toribio et al., "EAP as Multifunctional and Biomimetic Materials," SPIE Proceedings, Conference on Electroactive Polymer Actuators and Devices, Mar. 1999, vol. 3669, pp. 26-34.

Smela, Elisabeth, "Conjugated Polymer Actuators for Biomedical Applications," *Advanced Materials*, vol. 15, No. 6, Mar. 17, 2003, pp. 481-494.

Gülch, Ranier W., et al., "Characterization of Electroactive Behavior and of Progress in Developments and Applications of Ionic Polymer Gels," *Smart Structures and Materials 2002*, ed. Y. Bar-Cohen, SPIE Proceedings, vol. 4695, 2002, pp. 367-377.

Bar-Cohen, Yoseph, "Electroactive Polymers as Artificial Muscles—Capabilities, Potentials and Challenges," Sec. 11 in chap. 8 of *Handbook on Biomimetics*, ed. Yoshihito Osada (NTS, Inc., 2000), pp. 1-3.

Wax, S.G., et al., "Complaint Actuators Based on Electroactive Polymers," Materials Research Society Symposium Proceedings, vol. 600, 2000, pp. 3-11.

Rocchia, W., et al., "Exploiting Conducting Polymer Radial Expansion for Bioinspired Actuation," *Smart Structures and Materials 2003*, ed. Y. Bar-Cohen, SPIE Proceedings, vol. 5051, 2003, pp. 453-457.

Sahoo, Hemantkumar, et al., "Actuators Based on Electroactive Polymers," *Current Science*, vol. 81, No. 7, Oct. 2001, pp. 743-746.

Sansiñena, José-Maria, et al., "Conductive Polymers," Chap. 7 in *Electroactive Polymer Actuators (EAP) as Artificial Muscles*, ed. Y. Bar-Cohen (SPIE Press, 2001), pp. 193-221.

Bar-Cohen, Yoseph, ed., *WorldWide ElectroActive Polymers EAP (Artificial Muscles) Newsletter*, vol. 3, No. 1, Jun. 2001.

Bar-Cohen, Yoseph, "EAP History, Current Status, and Infrastructure,," Chap. 1 in *Electroactive Polymer Actuators (EAP) as Artificial Muscles*, ed. Y. Bar-Cohen (SPIE Press, 2001), pp. 3-43.

Kornbluh, Roy, et al., "Application of Dieelectric Elastomer EAP Actuators," Chap. 16 in *Electroactive Polymer Actuators (EAP) as Artificial Muscles*, ed. Y. Bar-Cohen (SPIE Press, 2001), pp. 457-495.

Bar-Cohen, Yoseph, "Transition of EAP Material from Novelty to Practical Applications—Are We There Yet?" *Smart Structures and Materials 2001*, ed. Y. Bar-Cohen, SPIE Proceedings, vol. 4329, 2001, pp. 1-6.

Pelrine, Ron, et al., "Applications of Dielectric Elastomer Actuators," *Smart Structures and Materials 2001*, ed. Y. Bar-Cohen, SPIE Proceedings, vol. 4329, 2001, pp. 335-349.

Madden, John D.W., et al., "Polyprrole Actuators: Modeling and Performance," *Smart Structures and Materials 2001*, ed. Y. Bar-Cohen, SPIE Proceedings, vol. 4329, 2001, pp. 72-83.

Bar-Cohen, Yoseph, "EAP Applications, Potential,and Challenges," Chap. 21 in *Electroactive Polymer Actuators (EAP) as Artificial Muscles*, ed. Y. Bar-Cohen (SPIE Press, 2001), pp. 615-659.

Jager, Edwin W.H., et al., "Microfabricating Conjugated Polymer Actuators," *Science*, vol. 290, Nov. 2000, pp. 1540-1545.

Smela, Elisabeth, et al., "Electrochemically Driven Polypyrrole Bilayers for Moving and Positioning Bulk Micromachined Silicon Plates," *Journal of Microelectromechanical Systems*, vol. 8, No. 4, Dec. 1999, pp. 373-383.

Smela, Elisabeth, et al., "Thiol-Modified Pyrrole Monomers: 1. Synthesis, Characterization, and Polymerization of 1-(2-Thioethyl)pyrrole and 3-(2-Thioethyl)pyrrole," *Langmuir*, vol. 14, 1998, pp. 2970-2975.

Smela, Elisabeth, "Microfabrication of Ppy Microactuators and Other Conjugated Polymer Polymer Devices," *Journal of Micromechanics and Microengineering*, vol. 9, 1999, pp. 1-18.

Immerstrand, C., et al., "Conjugated-Polymer Micro- and Milliactuators for Biological Applications," *Materials research Society Bulletin*, Jun. 2002, pp. 1-4.

Madden, John D.W., et al., "Conducting Polymer Actuators as Engineering Materials," *Smart Structures and Materials 2002*, ed. Y. Bar-Cohen, SPIE Proceedings, vol. 4695, 2002, pp. 176-190.

Zhou, D., et al., "Actuators for the Cochlear Implant," *Synthetic Materials*, vol. 135-136, 2003, pp. 39-40.

http://www.micromuscle.com.

Brock, David L., Review of Artificial Muscle Based on Contractile Polymers. Massachusetts Institute of Technology Artificial Intelligence Laboratories. http://www.a1.mit.edu/projects/muscle/papers/memo1330/memo1330.html.

Material: Conducting polymers, Dielectric elastomers, Piezoelectric materials. http://www.designinsite.dk/htmsider.

Artificial Muscle Transducers. http://www.erg.sri.com/automation/actuators.html.

Miniature Electroactive-Polymer Rakes. http://www.nasatech.com/Briefs/Oct01/NPO20613.html.

Electroactive polymer. Nano Bioelectronics & Systems Research Center. http://nanobio.snu.ac.kr/eng/research_5.html.

Polymers and Separations Research Lab (PolySep). Electroactive Polymers as Artificial Muscles—A Primer. http://polysep.ucla.edu/Research%20Advances/EAP/electroactive_polymers-asartifi.htm.

Aviation Research. You Decide. Electroactive Polymers 2: Ionic and Conductive Polymers. http://virtualskies.arc.nasa.gov/research/youDecide/ionic NConducPolym.html.

ElectroActive Polymers—EAPs. http://www.azom.com/details.asp?ArticleID=885.

http://www.darpa.mil/dso/trans/electropolymers/projects/EAP_Jan02_LJB.pdf.

* cited by examiner

ELECTROACTIVE POLYMER ACTUATED SHEATH FOR IMPLANTABLE OR INSERTABLE MEDICAL DEVICE

FIELD OF THE INVENTION

This invention relates to sheaths for use in connection with the implantation or insertion of medical devices, such as stents.

BACKGROUND OF THE INVENTION

In a typical percutaneous translumninal coronary angioplasty (PTCA) procedure, a guiding catheter is percutaneously introduced into the cardiovascular system of a patient and advanced through the aorta until the distal end of the catheter is in the ostium of the desired coronary artery. Using fluoroscopy, a guidewire is then advanced through the guiding catheter and across the site to be treated in the coronary artery. An over-the-wire balloon catheter is then advanced over the guide wire to the treatment site, and the balloon is expanded to reopen the artery. The over-the-wire catheter may have a guide wire lumen which is as long as the catheter, or it may be a rapid exchange catheter in which the guide wire lumen is substantially shorter than the catheter. As another alternative, a fixed wire device may also be used. This device features a guide wire that is affixed to the catheter and cannot be removed.

To help prevent arterial closure, repair dissection, and/or prevent restenosis, a physician can implant an intravascular prosthesis, for example, a stent, inside the artery at the treatment site. The stent may be, for example, a self-expanding stent or a balloon expandable stent. For the latter type, the stent is typically delivered on a balloon and the balloon is used to expand the stent. The self-expanding stents may be made of shape memory materials such as nitinol or of other designs that exhibit self-expansion characteristics.

In certain known stent delivery catheters, a stent (e.g., a coronary vascular stent or another type of stent, such as a peripheral vascular stent, a renal stent, a biliary stent, etc.) and an optional balloon are positioned at the distal end of the catheter. The stent and optional balloon are held down and covered by a delivery sheath. When the distal end of the catheter is in its desired location within the targeted body lumen, the sheath is retracted in a proximal direction on the catheter to expose the stent. After the sheath is removed, the stent is free to self-expand or be expanded with a balloon.

SUMMARY OF THE INVENTION

In a medical device deployment system that utilizes a retractable sheath, one problem that is frequently encountered is the frictional forces that are generated between the sheath and the underlying medical device (e.g., a stent) upon retraction. These forces can damage the underlying stent. For example, stent coatings may be formed from fragile materials and can be damaged upon retraction of the overlying sheath. These and other difficulties are addressed by the present invention.

According to an aspect of the present invention, a medical device delivery sheath is provided, which comprises an active member that volumetrically expands and contracts upon application of an appropriate electrical potential. The active member further comprises an electroactive polymer, for example, polypyrrole.

The delivery sheath can be formed using one or more active members. In one embodiment, a single active member is provided in the form of an annulus. The annular active member can further comprise conductive layer on its outside surface, for example, to function as an electrode for the active member and to direct the active member in a radially inward direction.

According to another aspect of the present invention, a medical device delivery system is provided which comprises: (a) an elongate body adapted for insertion into a body lumen, the elongate body having distal and proximal ends; (b) the above delivery sheath, wherein the delivery sheath is disposed over all or a portion of the elongate body and is adapted to cover at least a portion of a medical device, for example, a stent; and (c) a control unit electrically coupled to the active member and adapted to apply electrical potentials that are effective to volumetrically expand and contract the active member, thereby actuating the sheath.

The medical device delivery system also typically comprises a retraction mechanism for retracting the delivery sheath. The retraction mechanism can comprise, for example, an electroactive polymer actuator, a mechanical pull wire, or other system for axially displacing the delivery sheath.

According to another aspect of the present invention, a method for delivering a medical device to a lumen of a patient is provided. The method comprises: (a) providing the above medical device delivery system, wherein the medical device is disposed proximate the distal end of the elongate body and wherein the delivery sheath at least partially covers the medical device; (b) inserting the distal end of the elongate body into the lumen; and (c) operating the control unit to actuate the delivery sheath, thereby at least partially disengaging the delivery sheath from the medical device. In certain embodiments, the method further comprises: (a) retracting the delivery sheath from the medical device, for example, using a retraction mechanism like the above; and (b) disengaging the medical device from the elongate body.

An advantage of the present invention is that frictional forces are reduced between the delivery sheath and an underlying medical device upon retraction of the sheath. This allows for smoother retraction of the sheath with less axial force, and decreases the possibility that the underlying prosthesis will be damaged.

Another advantage of the present invention is that delivery sheaths are provided, which are lightweight, flexible, simple, and easily manufactured.

Additional embodiments and advantages of the invention will become readily apparent to those of ordinary skill in the art upon review of the following detailed description in which the preferred embodiments are set forth in detail.

DESCRIPTION OF THE SPECIFIC EMBODIMENTS

The present invention now will be described more fully hereinafter with reference to the accompanying drawings, in which preferred embodiments of the present invention are shown. This invention may, however, be embodied in different forms and is not to be construed as limited to the embodiments set forth herein.

The delivery sheaths of the present invention are actuated, at least in part, using electroactive polymers (EAPs). Electroactive polymers are polymers characterized by their ability to change shape in response to electrical stimulation.

The electroactive polymers that are typically used in connection with the present invention are ionic EAPs, more typically those EAPs that feature a conjugated backbone and have the ability to increase electrical conductivity under oxidation or reduction. Some commonly known EAPs are polypyrrole, polyaniline, polythiophenes, polyethylenedioxythiophene, poly(p-phenylene vinylene), polysulfone and polyacetylene. Polypyrrole, which is one of the most stable of these polymers under physiological conditions, is pictured below:

These EAPs are typically semi-conductors in their pure form. However, upon oxidation or reduction of the polymer, the electrical conductivity is understood to be changed from a semi-conductive regime to a semi-metallic regime. Such oxidation and reduction is believed to lead to a charge imbalance that, in turn, results in a flow of ions into or out of the material. These ions typically enter/exit the polymer from/into an ionically conductive electrolyte medium associated with the electroactive polymer.

It is well known that dimensional changes are effectuated in certain polymers by the mass transfer of ions into or out of the polymer. For example, in some polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses and strains. These characteristics are ideal for construction of the devices of the present invention. As used herein, active member "actuation" refers to either the expansion or the contraction of the active member.

Conductive EAPs also have a number of additional properties that make them attractive for use in the devices of the present invention, including the following: (a) they are lightweight, flexible, and easily manufactured; (b) small changes in potential (e.g., potential changes on the order of 1V) can be used to effect volume change; (c) EAP regions can be created using a variety of techniques, for example, electrodeposition; and (d) EAP regions can be patterned, for example, using photolithography, if desired.

Medical device delivery systems constructed in accordance with the present invention generally include an elongated catheter body, a medical device (e.g., a stent) positioned near the distal end of the catheter body, and a delivery sheath overlying the medical device. The delivery sheath holds down and covers the medical device.

The delivery sheath is an EAP-actuated delivery sheath that tightens and relaxes its hold on the underlying medical device depending upon the applied voltage. In this connection, the medical device delivery systems of the present invention generally comprise the following elements: (a) a source of electrical potential, (b) an active member comprising an electroactive polymer, (c) a counter electrode and (d) an electrolyte in contact with both the active member and the counter electrode.

The electrolyte, which is in contact with at least a portion of the surface of the active member, allows for the flow of ions and thus acts as a source/sink for the ions. The electrolyte may be, for example, a liquid, a gel, or a solid, so long as ion movement is allowed. Where the electrolyte is a liquid, it may be, for example, an aqueous solution containing a salt, for example, a KCl solution, an NaCl solution, a phosphate buffered solution, a sodium dodecylbenzene sulfonate solution, physiological fluid, and so forth. Where the electrolyte is a gel, it may be, for example, a salt-containing agar gel or polymethylmethacrylate (PMMA) gel. Where the electrolyte is a solid, it may be, for example, a polymer electrolyte.

The counter electrode may be formed from any suitable electrical conductor, for example, a conducting polymer, a conducting gel, or a metal, for example, stainless steel, gold or platinum. At least a portion of the surface of the counter electrode is typically in contact with the electrolyte, in order to provide a return path for charge.

As noted above, the EAP-containing active member contracts or expands in response to the flow of ions out of, or into, the same. Essentially any electroactive polymer that exhibits contractile or expansile properties may be used in connection with the various aspects of the invention, including those set for above.

In accordance with certain embodiments of the invention, the active member is a polypyrrole-containing active member. Polypyrrole-containing active members can be fabricated using a number of known techniques, for example, extrusion, casting, dip coating, spin coating, or electro-polymerization/deposition techniques. Polypyrrole-containing active regions can be patterned using lithographic techniques, if desired.

Various dopants can be used in connection with polypyrrole-containing active members, including large immobile anions and large immobile cations. According to one specific embodiment, the active member comprises polypyrrole (PPy) doped with dodecylbenzene sulfonate (DBS) anions. When placed in contact with an electrolyte containing small mobile cations, for example, Na⁺ cations, and when a current is passed between the polypyrrole-containing active member and the counter electrode, the cations are inserted/removed upon reduction/oxidation of the polymer, leading to expansion/contraction of the same. This process can be represented by the following equation:

where Na⁺ represents a sodium ion, e⁻ represents an electron, PPy⁺ represents the oxidized state of the polymer, PPy° represents the reduced state of the polymer, and species are enclosed in parentheses to indicate that they are incorporated into the polymer. In this case the sodium ions are supplied by the electrolyte (which can be, for example, an aqueous electrolyte, a gel electrolyte or a solid polymer electrolyte) that is in contact with the electroactive polymer member. When the EAP is oxidized, the positive charges on the backbone are at least partially compensated by the DBS⁻ anions present within the polymer. Upon reduction of the polymer, however, the immobile DBS⁻ ions cannot exit the polymer to maintain charge neutrality, so the smaller, more mobile, Na⁺ ions enter the polymer, expanding the volume of the same. Upon re-oxidation, the Na⁺ ions again exit the polymer into the electrolyte, reducing the volume of the polymer.

The source of electrical potential for use in connection with the present invention can be quite simple, consisting, for example, of a dc battery and an on/off switch. Alternatively, more complex systems can be utilized. For example, an electrical link and be established with a microprocessor, allowing a complex set of control signals to be sent to the EAP-containing active member(s) within the sheath. These more complex systems may be used, for example, where multiple active members are used to exert complex dimensional changes.

Depending upon the selection of the EAP, dopant, and electrolyte, for example, EAP-containing active regions can be provided that either expand or contract when an applied voltage of appropriate value is interrupted. Therefore, in some embodiments of the invention, the sheath formed from the EAP will tighten its grip on the underlying medical device when an applied electrical potential is interrupted, while in other embodiments, the sheath will loosen its hold.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science*, 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999; U.S. Pat. No. 6,249,076, assigned to Massachusetts Institute of Technology, and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Figure 1A:
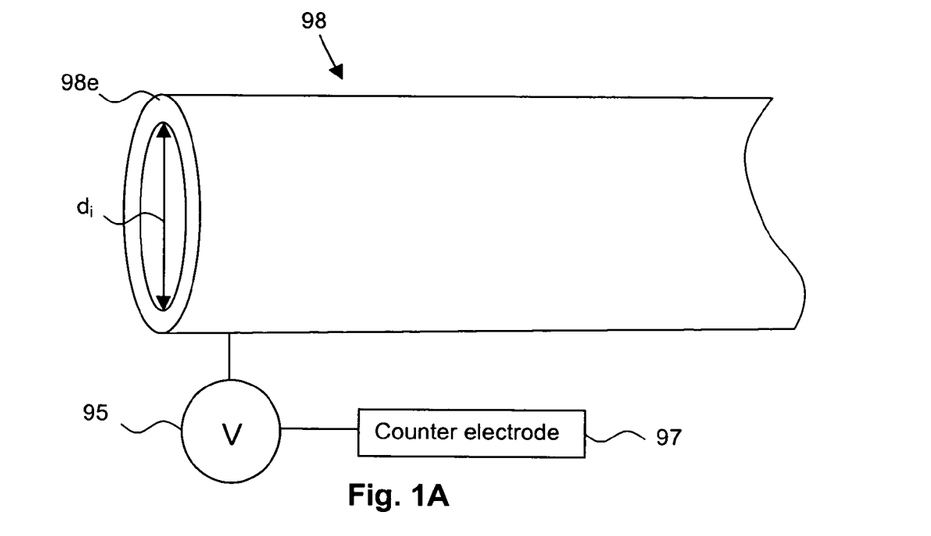
FIG. 1A is a schematic illustration of an electroactive-polymer-actuated delivery sheath in accordance with an embodiment of the present invention.

Turning now to the drawings, FIG. 1A is a schematic illustration of an EAP-actuated delivery sheath 98, in accordance with an embodiment of the present invention. The EAP actuated sheath 98 in this embodiment consists of an EAP-containing annular polymer region 98e. As noted above, a number of ionic EAPs are presently available for use in annular polymer region 98e. According to one embodiment, the electroactive polymer is a conjugated polymer, for example, polypyrrole (PPy), which is doped with a large immobile anion, for example, dodecylebenezene sulfonate (DBS). To change the dimensions of EAP-containing annular polymer region 98e, an electrical potential is applied between counter electrode 97 and EAP-containing annular polymer region 98e using voltage source 95. An electrolyte (not illustrated) containing small mobile cations such as Na⁺ (e.g., Na⁺DBS⁻ solution, Na⁺Cl⁻ solution, physiological fluid, etc.) is typically provided as a cation source/sink as discussed above. As the polymer is reduced, the cations are inserted, leading to expansion of the annular polymer region 98e and hence a reduction inner diameter $d_i$. As the polymer is oxidized, on the other hand, cations are removed, leading to contraction of the annular polymer region 98e and hence an enlargement in $d_i$.

Figure 1B:
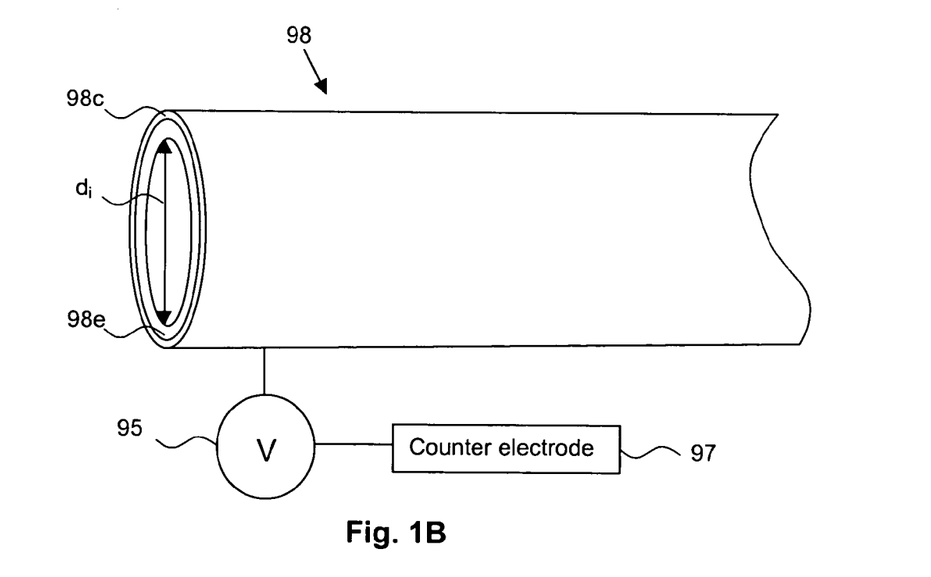
FIG. 1B is a schematic illustration of an EAP-actuated delivery sheath in accordance with another embodiment of the present invention.

FIG. 1B is a schematic illustration of an EAP-actuated delivery sheath 98, in accordance with another embodiment of the present invention. FIG. 1B is similar to FIG. 1A, with the exception that the EAP actuated sheath 98 in this embodiment comprises an annular conductive layer 98c outside the electroactive polymer layer 98e. The conductive layer 98c can be formed from essentially any conductive material. In one particular embodiment, the conductive layer 98c is a metal layer, for example, a gold or gold-plated layer, which is advantageous as it is resistant to corrosion and highly conductive, improving current distribution. Metal layers are also relatively inelastic, forcing the expanding electroactive polymer layer 98e into tighter engagement with an underlying medical prosthesis upon expansion of the polymer layer 98e. Flexibility can be introduced by providing the conductive layer 98c in the form of a thin foil. As in FIG. 1A, the EAP-containing annular polymer region 98e can be expanded to reduce the inner diameter $d_i$, or contracted to enlarge $d_i$.

The use of an EAP actuated sheath 98 of the present invention in connection with a stent delivery system will now be described with reference to FIGS. 2A and 2B. It is noted that, although this system is for the delivery of a self-expanding stent, the EAP actuated sheaths in accordance with the present invention are useful in connection with a wide variety of medical devices, including endovascular stent grafts, vena cava filters, balloon expandable stents (including coronary stents, peripheral vascular stents, renal stents, biliary stents, etc.), embolic coils, valve replacement devices, septal defect devices, radiofrequency treatment devices, cryogenic treatment devices, and the like.

Figure 2A:
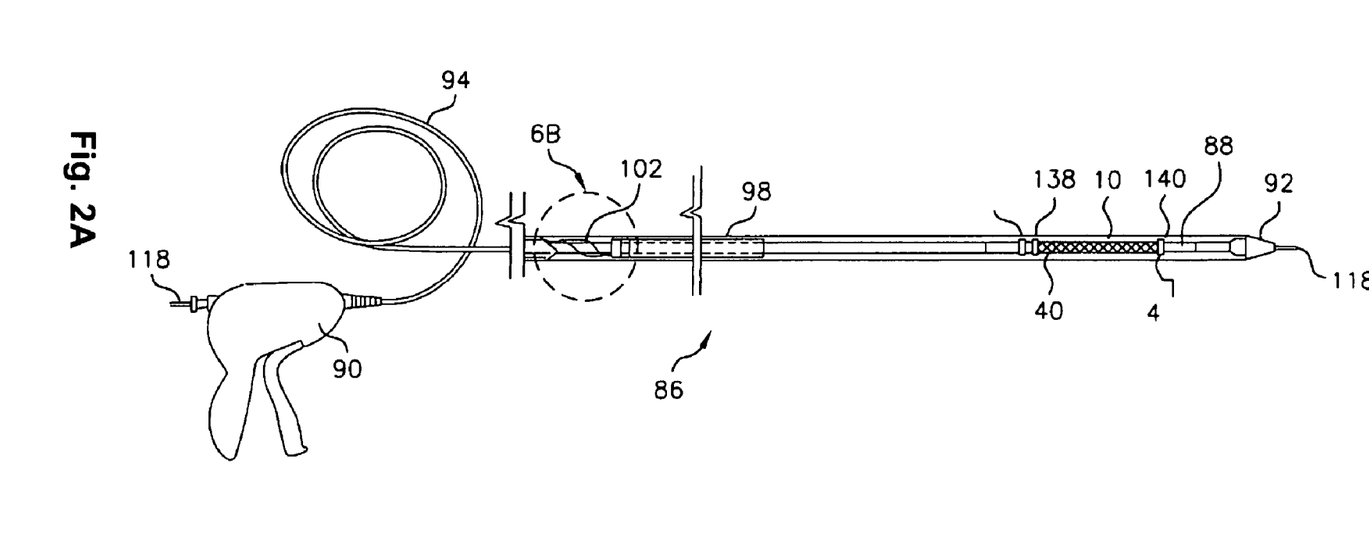
FIG. 2A is an illustration of an over-the-wire delivery system comprising an electroactive-polymer-actuated delivery sheath in accordance with an embodiment of the present invention.
Figure 2B:
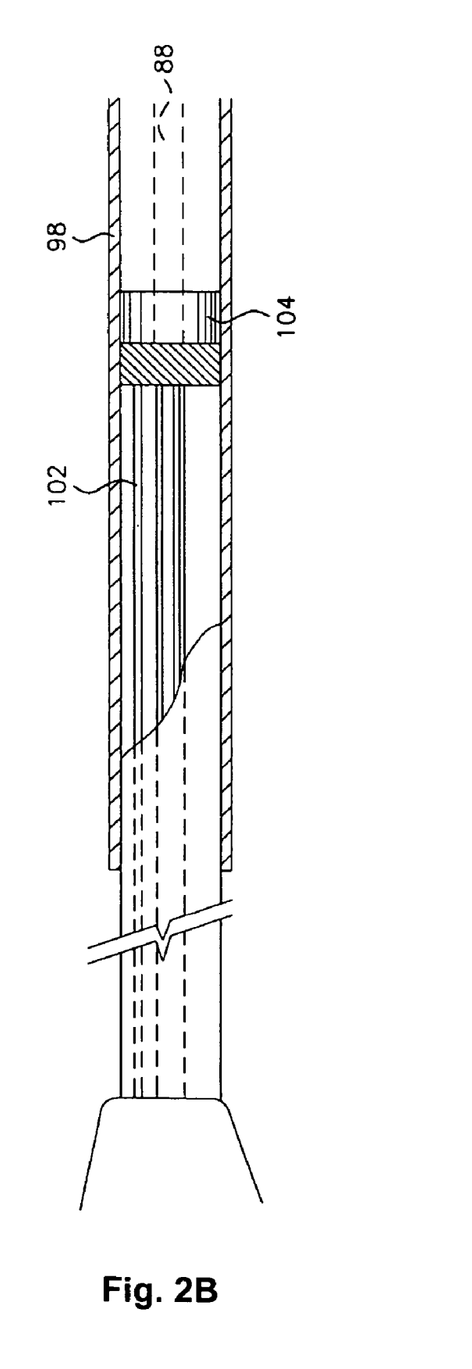
FIG. 2B is an enlarged view of the middle section of the over-the-wire delivery system of FIG. 2A.

Turning now to FIGS. 2A and 2B, an over-the-wire delivery system 86 is illustrated for inserting a self-expanding stent 10 into a body lumen. The over-the-wire delivery system 86 includes an elongated catheter body built upon inner shaft 88 over which the stent 10 is positioned. The shaft 88 extends from a proximal handle 90 to a distal tip end 92. The inner shaft 88 extends through an outer shaft 94 at the proximal end. A guidewire 118 extends through the catheter to the distal end tip 92. In the embodiment illustrated, markers 138 and 140 are located at opposite ends of the stent 10, to mark the proximal and distal ends of the stent 10 when in its compressed delivery position. If desired, these markers could also be positioned to correspond to the proximal and distal ends of the stent 10 in its expanded position as well. (The length of the stent 10 in its compressed delivery configuration is typically slightly longer than it is when expanded.)

An EAP actuated delivery sheath 98 in accordance with the present invention is located at the distal end of the over-the-wire delivery system 86. In the particular embodiment illustrated, the delivery sheath 98 is designed to flush fit with distal end tip 92 during advancement along the body lumen to create a substantially smooth profile. Although not illustrated, the EAP actuated delivery sheath 98 is also commonly provided with a hydrophilic coating to increase lubricity.

As noted above, expansion and contraction of the delivery sheath 98 typically requires (a) a source of electrical potential, (b) an active member comprising an electroactive polymer, (c) a counter electrode, and (d) an electrolyte disposed between the active member and the counter electrode. The source of electrical potential (e.g., a battery, not illustrated) can be provided essentially anywhere in the system. A simple switch can be used to control the application of the electrical potential between the EAP-containing active member and the counter electrode as previously noted. For example, such a switch (not illustrated) may be provided at handle 90. The counter electrode (not illustrated) can be, for example, a dedicated conductive member within the delivery system 86. Alternatively, a conductive element of the delivery system 86 itself can be used for this purpose. In either case, care should be taken to avoid electrically shorting the electroactive polymer region with the counter electrode. The electrolyte can be provided, for example, within a sealed structure that also encloses the active member and counter electrode. Alternatively, a fluid supplied by the delivery system (e.g., saline) or ambient physiological fluid can function as the electrolyte.

During loading, the self expanding stent 10 is compressed at low temperature and held in its compressed delivery configuration by the delivery sheath 98. Using the delivery sheath 98 design of FIG. 1A as an example, the EAP-containing annular polymer region 98*e* is typically positioned over the stent 10 during loading, while in a contracted state. Subsequently, the EAP-containing annular polymer region 98*e* is expanded, thereby tightening the engagement between the sheath 98 and the stent 10. Once an appropriate delivery position is reached, the EAP-containing annular polymer region 98*e* is again contracted, loosening the engagement between the sheath 98 and the stent 10. EAP actuated sheath 98 is then moved towards the handle 90 using pull wire 102 connected to pull ring 104, which is in turn is connection to EAP actuated sheath 98 as seen in FIG. 2B. By contracting the EAP-containing annular polymer region 98*e*, the frictional force between the inner wall of the EAP actuated sheath 98 and the catheter and stent is reduced, allowing a smoother retraction of the EAP actuated sheath 98 with less required axial force. For example, measurements have indicated that nitinol self-expanding stents undergo an approximately 50% drop-off in radial outward force within the first 17% of stent diameter increase. Accordingly, a small increase in the inside diameter $d_i$ of the sheath 98 can yield a large improvement in frictional force.

Figure 3:
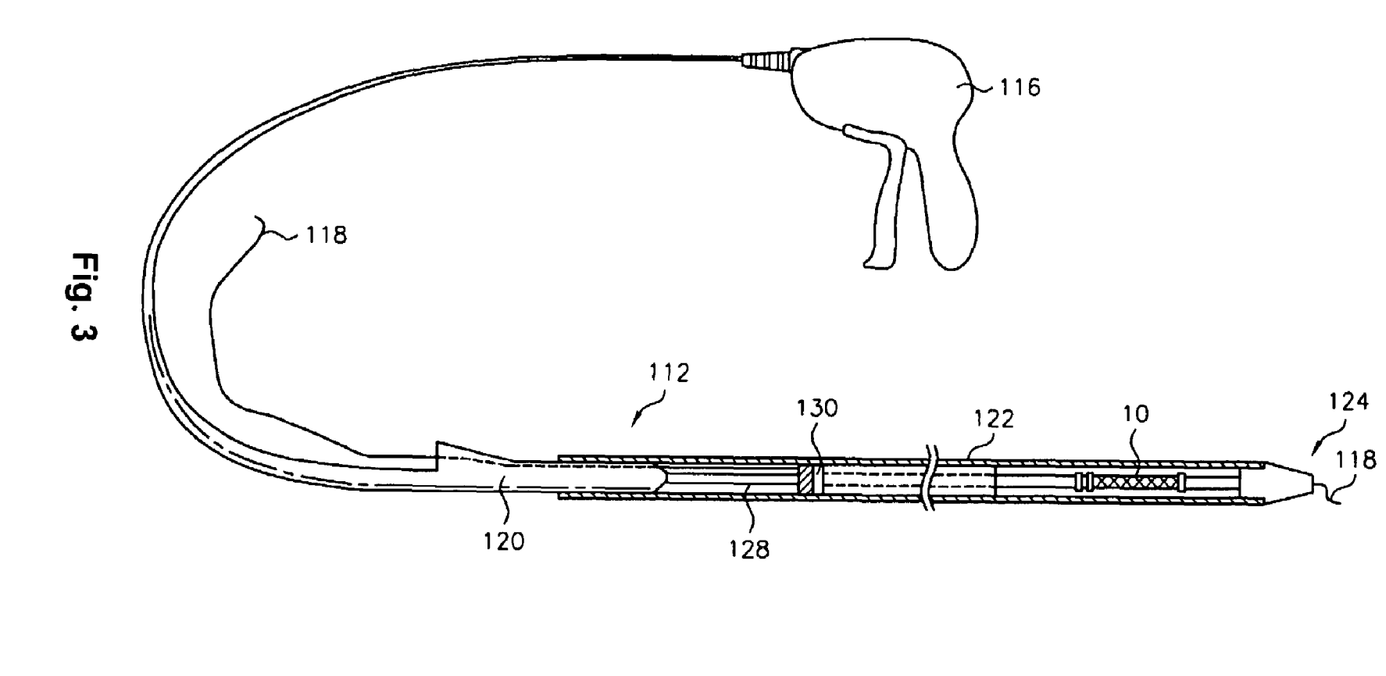
FIG. 3 is an illustration of a rapid exchange delivery system comprising an electroactive-polymer-actuated delivery sheath in accordance with an embodiment of the present invention.

An alternative to the over-the-wire delivery system 86 shown in FIGS. 2A and 2B is a rapid exchange delivery system 112 shown in FIG. 3. The rapid exchange delivery system 112 has a proximal handle 116. A guidewire 118 extends from a two lumen transition zone 120 through an outer EAP actuated sheath 122 to a distal tip end 124. In contrast to the over-the-wire delivery system 86, the guide wire 118 does not extend all the way back to the proximal handle 116. Similar to the over-the-wire delivery system 86, the outer EAP actuated sheath 122 of the rapid exchange delivery system 112 is moved towards the handle 116 using a pull wire 128 and a pull ring 130.

Use of the over-the-wire delivery system 86 of FIGS. 2A and 2B for delivery of a stent 10 to a body lumen will now be briefly described, in accordance with an embodiment of the invention. First, a lumen obstruction is located using one of several diagnostic techniques. The physician then gains access to the lumen, and using an appropriate diagnostic technique such as ultrasound or fluoroscopy, the guidewire 118 is maneuvered through the body lumen so that it extends past the obstruction. The delivery system 86, with preloaded medical device (a self-expanding stent 10 in this embodiment), is then passed through an introducer sheath and tracked over the guidewire 118 until the distal marker 140, which indicates the position of the distal end 47 of the stent 10, is positioned at a location that is distal of the occlusion. Marker 138 indicates the position of the proximal end 40 of the stent 10. In general, the stent 10 is centered about the obstruction.

The EAP actuated sheath 98 is then disengaged from the delivery system, for example, by first contracting the EAP-containing annular polymer region 98*e* (when using a sheath 98 design like that illustrated in FIG. 1), followed by proximal retraction of sheath 98 using pull wire 102 as discussed above. Upon deployment in vivo at body temperature, the original stent shape is restored as the nitinol stent 10 self-expands, exerting radial force on the constricted portion of the body lumen, re-establishing patency of the lumen, and firmly anchoring the stent so that it resists axial motion. The stent 10 is then completely separated from the catheter body by drawing the catheter body proximally. The catheter body is then removed from the body, leaving the prosthesis 10 positioned in the body lumen.

Numerous additional designs can be utilized when constructing EAP actuated sheaths in accordance with the present invention. For example, multiple EAP-containing active regions or multiple distinct electroactive polymer actuators can be utilized.

Figure 4:
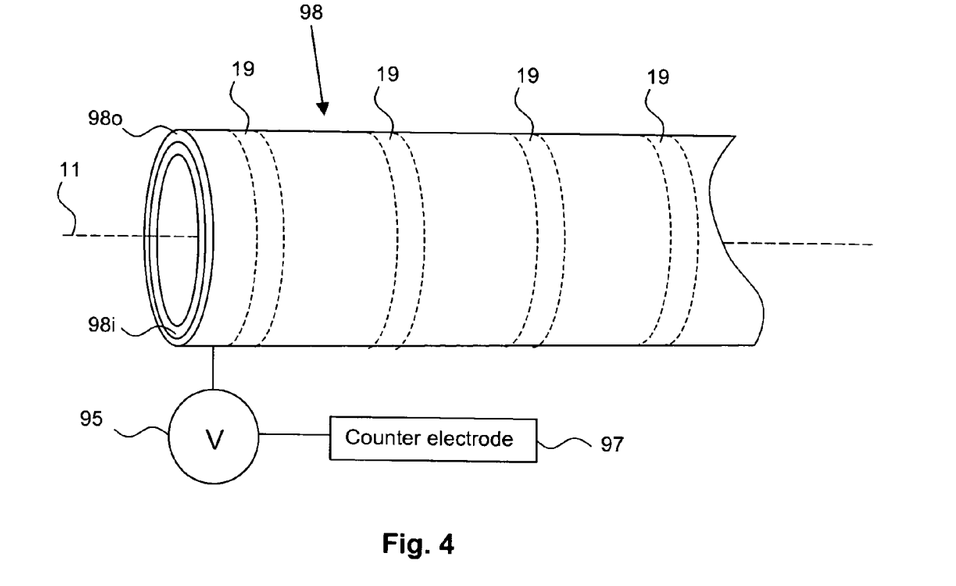
FIG. 4 is a schematic illustration of an electroactive-polymer-actuated delivery sheath in accordance with another embodiment of the present invention.

For instance, an electroactive polymer sheath 98, in accordance with another embodiment of the invention, is schematically illustrated in FIG. 4. In this embodiment, electroactive polymer sheath 98 includes inner layer 98*i* and outer layer 98*o*. Between layers 98*i* and 98*o* are disposed a series of linearly expanding and contracting electroactive polymer actuators 19, which at least partially wrap around the longitudinal axis 11 of the sheath 98. The inner layer 98*i* in this embodiment is constructed of a material that is sufficiently pliable to allow the sheath 98 to firmly engage the underlying medical device upon axial contraction of the actuators 19.

Figure 5:
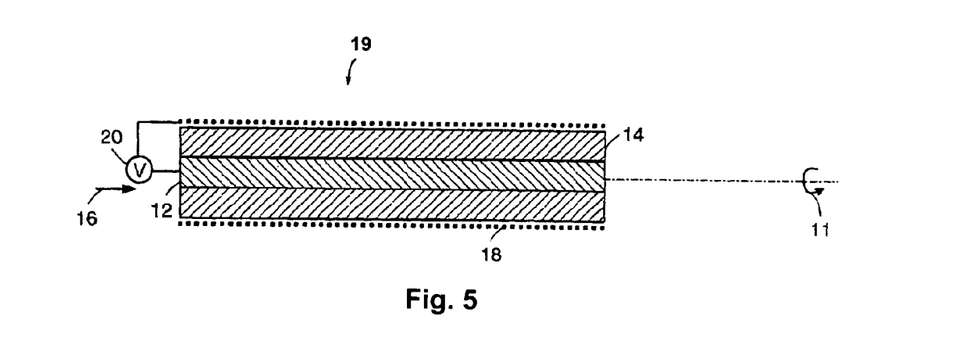
FIG. 5 is a schematic cross-sectional view of an electroactive polymer actuator.

Referring now to FIG. 5, a single linearly expanding and contracting actuator 19 is illustrated schematically in cross-section. Active member 12 of actuator 19 has a surface coupled with electrolyte 14 and has an axis 11. Active member 12 includes an electroactive polymer that contracts or expands in response to the flow of ions out of or into the active member 12. Ions are provided by electrolyte 14, which adjoins member 12 over at least a portion, and up to the entirety, of the surface of active member 12 in order to allow for the flow of ions between the two media. Various geometries are available for the relative disposition of member 12 and electrolyte 14. In accordance with some embodiments of the invention, member 12 may be a film, a group of films, a fiber, a group of fibers, or a combination of the same, disposed so as to apply a force in a longitudinal direction substantially along axis 11. Electrolyte 14 may be, for example, a liquid, a gel, or a solid, as discussed above. Counter electrode 18 is in electrical contact with electrolyte 14 in order to provide a return path for charge to a source 20 of potential difference between member 12 and counter electrode 18. Counter electrode 18 may be any suitable electrical conductor, as previously noted. Counter electrode 18 is in the form of a coil in FIG. 5, but other configurations are possible. In order to activate the actuator 10, a current is passed between active member 12 and counter electrode 18, inducing contraction or expansion of member 12. An electroactive polymer actuator of this type is described, for example, in U.S. Pat. No. 6,249,076, assigned to Massachusetts Institute of Technology.

In other embodiments of the invention, electroactive polymer actuation is also used to retract the delivery sheath 98, rather than using a pull wire as above. For example, an electroactive polymer actuator 19 like that illustrated in FIG. 5 may be used to exert an axial retractive force upon the pull-back sheath 98. Alternatively, electroactive polymer actuators can be configured to hinge, as in a bellows, to exert a retractive force.

In still other embodiments, a delivery sheath is provided, which both radially expands and axially contracts to both release and retract from the enclosed medical device. For example a plurality of electroactive polymer strips or fibers may be included within the sheath to effect both radial and axial forces upon activation. These strips or fibers may be included in a woven or braided configuration, if desired.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device delivery sheath comprising an active member that volumetrically expands and contracts, said active member further comprising an electroactive polymer.

2. The medical device delivery sheath of claim 1, wherein said active member is an annular active member.

3. The medical device delivery sheath of claim 2, wherein said sheath comprises an electrically conductive annular layer outside of said annular active member.

4. The medical device delivery sheath of claim 1, wherein said delivery sheath comprises a plurality of active members.

5. The medical device delivery sheath of claim 1, wherein said electroactive polymer comprises polypyrrole.

6. A medical device delivery system comprising: an elongate body adapted for insertion into a body lumen, said elongate body having distal and proximal ends; the medical device delivery sheath of claim 1, wherein said delivery sheath is disposed over said elongate body and is adapted to cover at least a portion of a medical device; and a control unit electrically coupled to said active member and adapted to apply electrical potentials that are effective to volumetrically expand and contract said active member, thereby actuating said sheath.

7. The medical device delivery system of claim 6, wherein said active member is an annular active member.

8. The medical device delivery system of claim 7, wherein said sheath comprises an electrically conductive annular layer outside of said annular active member.

9. The medical device delivery system of claim 6, wherein said delivery sheath comprises a plurality of active members.

10. The medical device delivery system of claim 6, wherein said electroactive polymer comprises polypyrrole.

11. The medical device delivery system of claim 6, wherein said medical device is a stent.

12. The medical device delivery system of claim 6, wherein said control unit comprises a dc power source and an on/off switch.

13. The medical device delivery system of claim 6, wherein said control unit comprises a microprocessor.

14. The medical device delivery system of claim 13, wherein said delivery sheath comprises a plurality of active members.

15. The medical device delivery system of claim 14, wherein said active members are independently actuated.

16. The medical device delivery system of claim 6, wherein said system comprises a retraction mechanism for retracting said delivery sheath.

17. The medical device delivery system of claim 16, wherein said retraction mechanism comprises an electroactive polymer actuator.

18. The medical device delivery system of claim 16, wherein said retraction mechanism comprises a pull wire.

19. The medical device delivery system of claim 6, further comprising said medical device.

20. The medical device delivery system of claim 19, wherein said medical device is a stent.

21. A method for delivering a medical device to a lumen of a patient comprising:
providing the medical device delivery system of claim 19, wherein said medical device is disposed proximate said distal end of said elongate body and wherein said delivery sheath at least partially covers said medical device; inserting said distal end of said elongate body into said lumen; and operating said control unit to actuate said delivery sheath, thereby at least partially disengaging said delivery sheath from said medical device.

22. The method of claim 21, further comprising: retracting said delivery sheath from said medical device; and disengaging said medical device from said elongate body.

23. The method of claim 22, wherein said medical device is a stent.

* * * * *

UNITED STATES PATENT AND TRADEMARK OFFICE
CERTIFICATE OF CORRECTION

PATENT NO.       : 7,338,509 B2
APPLICATION NO.  : 10/702314
DATED            : March 4, 2008
INVENTOR(S)      : Richard Carlton Mattison It is certified that error appears in the above-identified patent and that said Letters Patent is hereby corrected as shown below:

Col. 1, line 13, after "percutaneous", "translumninal" to --transluminal--.

Col. 1, line 21, after "the", first occurrence, change "guide wire" to --guidewire--.

Col. 1, line 23, after "a", change "guide wire" to --guidewire--.

Col. 1, line 25, change first word "guide wire" to --guidewire--.

Col. 1, line 27, after "a", change "guide wire" to --guidewire--.

Col. 5, line 14, change equation "$PPy^+(DBS^-)+Na^++e^-PPy^o(Na^+DBS^-)$" to

--$PPy^+(DBS^-)+Na^++e^- \rightarrow PPy^o(Na^+DBS^-)$--.

Col. 5, line 37, after "link", change "and" to --can--.

Col. 6, line 20, after "reduction", add --in--.

Col. 7, line 50, after first word "turn", change "is connection" to --connected--.

Col. 7, line 67/Col. 8, line 1, change last/first words "guide wire" to --guidewire--.

Signed and Sealed this

Second Day of September, 2008

JON W. DUDAS
*Director of the United States Patent and Trademark Office*